(12) United States Patent
Razi

(10) Patent No.: US 7,585,503 B2
(45) Date of Patent: Sep. 8, 2009

(54) METHOD FOR DETECTING MULTI-DRUG RESISTANCE

(76) Inventor: Nahid Razi, 8241 La Jolla Scenic Dr. North, La Jolla, CA (US) 92037

(*) Notice: Subject to any disclaimer, the term of this patent is extended or adjusted under 35 U.S.C. 154(b) by 0 days.

(21) Appl. No.: 11/094,704

(22) Filed: Mar. 31, 2005

(65) Prior Publication Data

US 2006/0223128 A1    Oct. 5, 2006

(51) Int. Cl.
*A61K 39/395* (2006.01)
(52) U.S. Cl. ......................... 424/133.1; 514/8
(58) Field of Classification Search ............ None
See application file for complete search history.

(56) References Cited

U.S. PATENT DOCUMENTS

2002/0042079 A1* 4/2002 Simon et al. ............ 435/7.1

OTHER PUBLICATIONS

Zips d, Thames HD, Baumann M. New Anticacner Agents: In Vitro and In Vivo Evaluation. In Vivo. Jan.-Feb. 2005;19(1):1-7.*
Fiala et al. Biochimica et Biophysica Acta. vol. 1639, p. 213-224, Nov. 2003.*
Vierbuchen et al. Cancer. vol. 76(5), p. 727-735, 1995 (Abstract only).*
Mayer et al. Cancer and Metastasis Reviews vol. 20, p. 87-93 2001.*
Ban et al. "Surface Coat of Plasma Membrane of L—1210 Lymphoid Leukemia Cells. A Cytochemical Study" Polia Histochemica et Cytochemica, vol. 19, No. 1, 1981, pp. 3-10.

* cited by examiner

*Primary Examiner*—Larry R. Helms
*Assistant Examiner*—Meera Natarajan
(74) *Attorney, Agent, or Firm*—Knobbe Martens Olson & Bear, LLP

(57) ABSTRACT

The present invention stems from the realization that the cell surface content of sialic acids is associated with drug susceptibility and resistance in neoplastic and damaged cells. A general decrease in the amounts of the α2-6 linked sialic acid has been confirmed in resistant phenotype compare to its corresponding sensitive parental cells. Treating the resistant phenotype with neuraminidase, an enzyme that removes the sialic acid from the sugar chain, facilitates the drug internalization and reinstalls the cell susceptibility to the drug. Based on these observations, methods for predicting the resistance to a number of drugs and detecting multi-drug resistanc in neoplastic and damaged cells have been invented.

22 Claims, 8 Drawing Sheets

SNA binding to Sia α 2,6 linkage

SNA binding to 2008 isotypes:
Susceptible (light gray)
Resistant (dark gray)
Background (Thin black)

SNA binding to IGROV-1 isotypes:
Susceptible (light gray)
Resistant (dark gray)
Background (Thin black)

SNA binding to A2780 isotypes:
Susceptible (light gray)
Resistant (dark gray)
Background (Thin black)

MAA binding to Sia α 2-3 linkage

MAA staining of IGROV-1 isotypes:
Susceptible (light gray)
Resistant (dark gray)
Background (Thin black)

FIG. 4A

MAA staining of A2780 isotypes:
Susceptible (light gray)
Resistant (dark gray)
Background (Thin black)

FIG. 4B

MAA staining of 2008 isotypes:
Susceptible (light gray)
Resistant (dark gray)
Background (Thin black)

FIG. 4C

ECA binding to LacNAc/GalNAc

ECA binding to 2008 isotypes:
Susceptible (light gray)
Resistant (dark gray)
Background (Thin black)

ECA binding to IGROV-1 isotypes:
Susceptible (light gray)
Resistant (dark gray)
Background (Thin black)

ECA binding to A 2780 isotypes:
Susceptible (light gray)
Resistant (dark gray)
Background (Thin black)

PNA binding to Gal β1,3 GalNAc

PNA binding to A2780 isotypes:
Susceptible (light gray)
Resistant (dark gray)
Background (Thin black)

PNA binding to 2008 isotypes:
Susceptible (light gray)
Resistant (dark gray)
Background (Thin black)

PNA binding to IGROV-1 isotypes:
Susceptible (light gray)
Resistant (dark gray)
Background (Thin black)

Galectin-1 detected by anti galectin-1 antibody

Galectin-1 staining of 2008 isotypes:
Susceptible (light gray)
Resistant (dark gray)
Background (Thin black)

Galectin-1 staining of IGROV-1 isotypes:
Susceptible (light gray)
Resistant (dark gray)
Background (Thin black)

Galectin-1 staining of A 2780 isotypes:
Susceptible (light gray)
Resistant (dark gray)
Background (Thin black)

Galectin-4 detected by anti galectin-4 antibody

Galectin-4 staining of 2008 isotypes:
Susceptible (light gray)
Resistant (dark gray)
Background (Thin black)

Galectin-4 staining of IGROV-1 isotypes:
Susceptible (light gray)
Resistant (dark gray)
Background (Thin black)

Galectin-4 staining of A 2780 isotypes:
Susceptible (light gray)
Resistant (dark gray)
Background (Thin black)

METHOD FOR DETECTING MULTI-DRUG RESISTANCE

FIELD OF THE INVENTION

The present invention relates to predicting multi-drug resistance and detecting multi-drug resistant cells.

BACKGROUND OF THE INVENTION

Resistance to cytotoxic agents is a common clinical problem in the treatment of neoplastic or damaged cells. "Multi-drug resistant" and "multidrug resistance" (MDR) are referred to, in a neoplastic cell or damaged cell, resistance to a number of different drugs. Such cells have reduced efficacy of all the drugs concerned, including drugs to which the neoplastic cell or damaged cell was never exposed. MDR cells commonly exhibit a decrease in drug accumulation due to reduced uptake and increased efflux in resistant cells. Patients carrying MDR cells are often treated with drugs without an effective result. This has always been a dilemma in therapeutic management and selecting the appropriate strategy for treatments. Therefore, there is a need in the art to detect MDR cells such that the treatment for curing a patient carrying such cells may be adjusted to allow a predication of the effectiveness of the treatment and possibly improve the condition of the cells for increasing the up take of the concerned drugs into the cells.

DESCRIPTION OF THE DRAWINGS

FIG. (1): Depicts deconvoluting digital microscopy—Distribution of fluorescent-cisplatin (F-DDP) in the ovarian carcinoma cells resistant to cisplatin (treated with F-DDP). The resistant subline of the ovarian carcinoma (2008-C13*5.25) was incubated with 2 μmol/L of F-DDP for 1 hr and then stained for filamentous actin with Alexa Flour 647 phalloidin and with Hoechst 33342 for nuclei prior to being imaged for F-DDP accumulation. After removing the drug and washing the cells with cold-PBS, cells were fixed with formaldehyde and studied by digital deconvoluting fluorescent microscopy. The results show the merging of the F-DDP (C) and the filamentous actin (D) staining at the cell membrane in resistant cells (A) and (B).

FIG. (2): Depicts deconvoluting digital microscopy—Distribution of fluorescent-cisplatin (F-DDP) in the ovarian carcinoma cells resistant to cisplatin (concomitantly treated with cisplatin and sialidase). The resistant subline of the ovarian carcinoma (2008-C13*5.25) was incubated with 2 μmol/L of F-DDP and 5 mU of neuraminidase for 1 hr and then stained for filamentous actin with Alexa Flour 647 phalloidin and with Hoechst 33342 for nuclei prior to being imaged for F-DDP accumulation. After removing the drug and washing the cells with cold-PBS, cells were fixed with formaldehyde and studied by digital deconvoluting fluorescent microscopy. No accumulation of F-DDP was observed at the cell membrane and the overlapping F-DDP (C) and filamentous actin staining (D) disappeared, implying the F-DDP internalization (A) and (B).

FIG. (3): Depicts Fluorescent Activated Cell Sorting (FACS)—Detection of the cell surface α2-6 linked sialic acids in carcinoma isotype cell pairs of sensitive to cisplatin and their corresponding resistant phenotype. Cells were detached from the plates by mild trypsinization. After washing three times with ice-cold PBS containing 0.02% Na-Azide, cells were incubated, in the same buffer, with SNA-FITC for one hour to detect the cell surface α2-6 linked sialic acids. Binding of the lectin to the cells was detected by single-color flow cytometry. Panel (A) illustrates the SNA binding to 2008 and 2008 C13*5.25 isotypes, susceptible and resistant to cisplatin, respectively. Panel (B) illustrates the SNA binding to IGROV-1 and IGROV-1/CP susceptible and resistant isotypes, respectively. Panel (C) shows the SNA binding to A2780 and A2780/CP susceptible and resistant isotypes, respectively.

FIG. 4: Depicts Fluorescent Activated Cell Sorting (FACS)—Detection of the cell surface α2-3 linked sialic acids in carcinoma isotype cell pairs sensitive to cisplatin and their corresponding resistant phenotype. Cells were treated as described in FIG. 3, except for using MAA-FITC to detect the α2-3 linked sialic acids on the cells. Panel (A) illustrates the MAA binding to IGROV-1 and IGROV-1/CP susceptible and resistant isotypes, respectively. Panel (B) illustrates the MAA binding to A2780 and A2780/CP isotypes susceptible and resistant to cisplatin respectively. Panel (C) shows the MAA binding to 2008 and 2008 C13*5.25 isotypes susceptible and resistant to cisplatin, respectively.

Figure 5A:
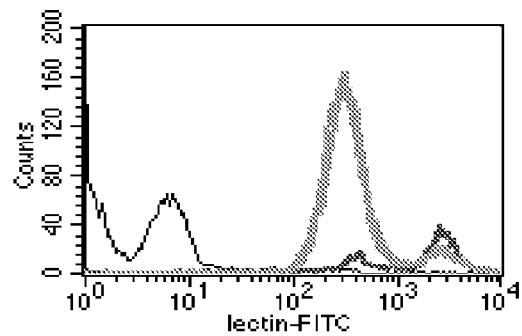
Figure 5B:
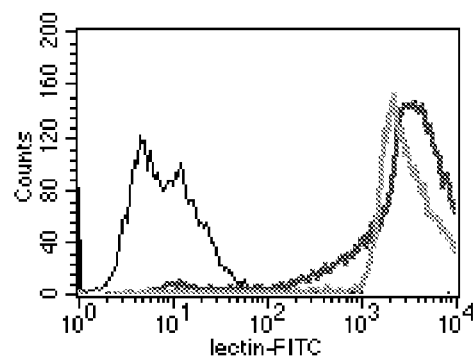
Figure 5C:
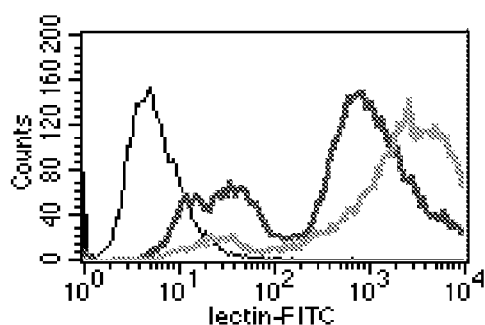

FIG. 5: Depicts Fluorescent Activated Cell Sorting (FACS)—Detection of the cell surface Lactosamin/Galactosamin in carcinoma isotype cell lines sensitive to cisplatin and their corresponding resistant phenotype. Cells were treated as described in FIG. 3 except for using ECA-FITC to detect the LacNAc/GalNAc on the cells. Panel (A) illustrates the ECA binding to 2008 and 2008 C13*5.25 isotype pair of susceptible and resistant to cisplatin, respectively. Panel (B) illustrates the ECA binding to IGROV-1 and IGROV-1/CP isotype pairs of susceptible and resistant to cisplatin, respectively. Panel (C) shows the ECA binding to A2780 and A2780/CP isotypes susceptible and resistant to cisplatin, respectively.

Figure 6A:
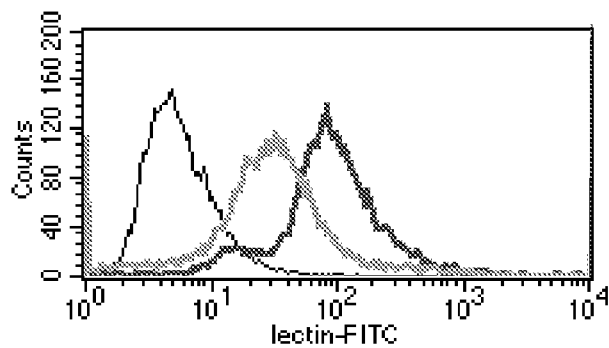
Figure 6B:
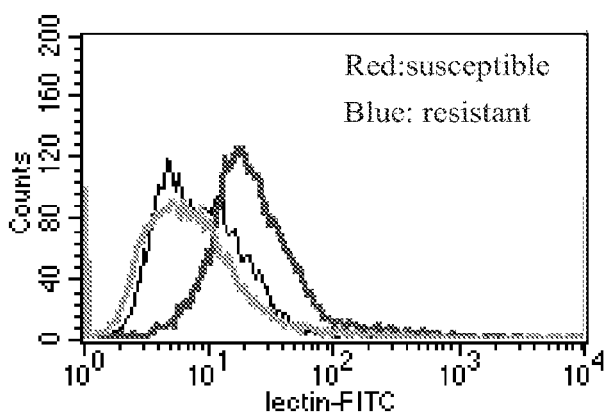
Figure 6C:
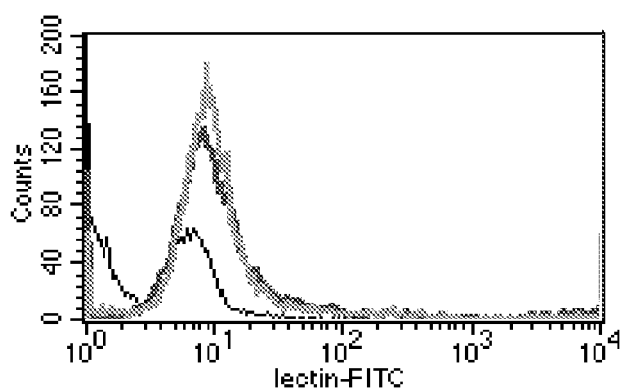

FIG. 6: Depicts Fluorescent Activated Cell Sorting (FACS)—Detection of the cell surface Galβ1-3GalNAc in carcinoma isotype cell lines sensitive to cisplatin and their corresponding resistant phenotype. Cells were treated as described in FIG. 3 except for using PNA-FITC to detect the Gal β1-3GalNAc on the cells. Panel (A) illustrates the PNA binding to A2780 and A2780/CP isotypes susceptible and resistant to cisplatin, respectively. Panel (B) illustrates the PNA binding to 2008 and 2008 C13*5.25 isotype pair of susceptible and resistant to cisplatin, respectively. Panel (C) shows the PNA binding to IGROV-1 and IGROV-1/CP isotypes susceptible and resistant to cisplatin, respectively.

Figure 7A:
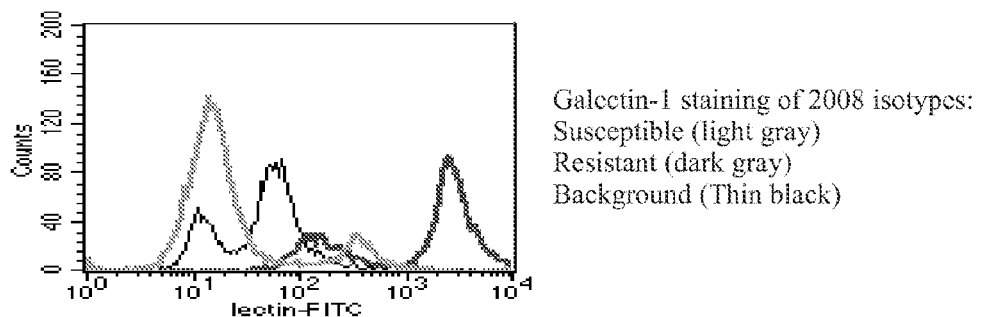
Figure 7B:
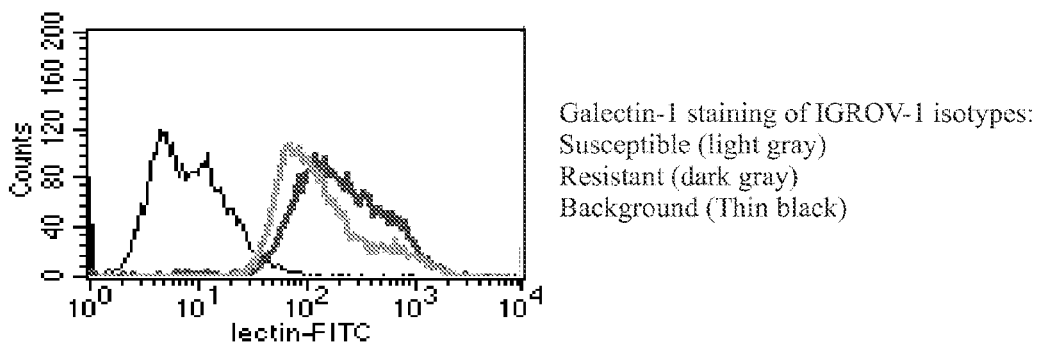
Figure 7C:
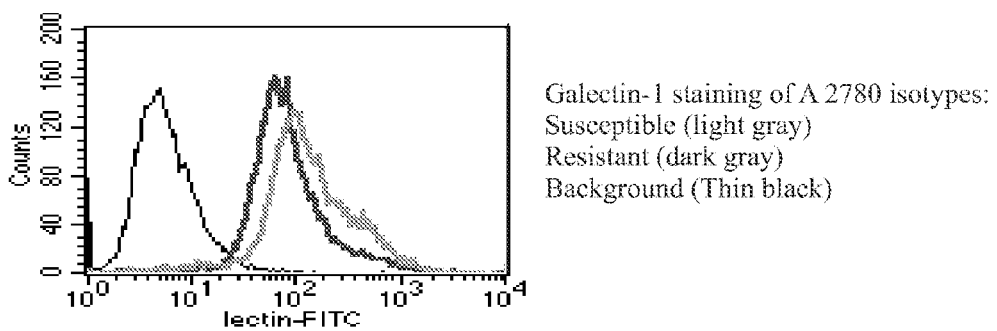

FIG. 7: Depicts Flow cytometry of Galectin-1 staining with the polyclonal anti galectin-1 antibody. Cells were treated as described in FIG. 3 except for using anti galectin-1 polyclonal antibody, which was then detected by a fluorescent conjugated secondary molecule. The mouse anti-rabbit immunoglobulin (mIg-FITC) was used to detect the anti-galectin-1 rabbit polyclonal antibody. Panel (A) shows the anti galectin-1 binding to 2008 and 2008 C13*5.25 isotypes susceptible and resistant to cisplatin, respectively. Panel (B) shows the binding of anti galectin-1 to IGROV-1 and IGROV-1/CP isotypes susceptible and resistant to cisplatin, respectively. Panel (C) shows the binding of anti galectin-1 to A2780 and A2780/CP isotypes susceptible and resistant to cisplatin, respectively.

Figure 8A:
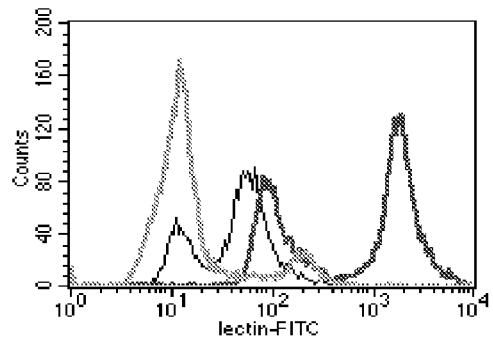
Figure 8B:
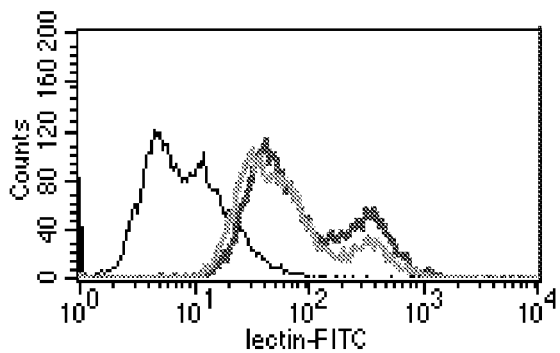
Figure 8C:
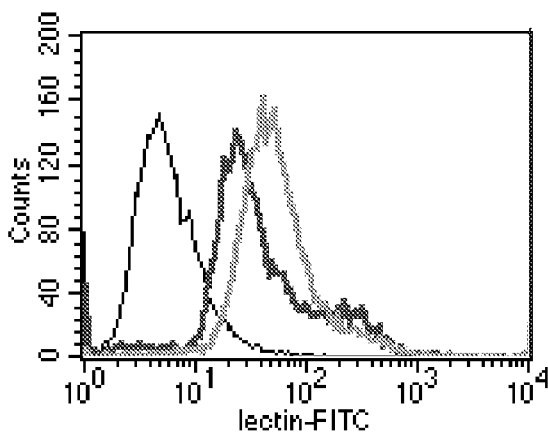

FIG. 8: Depicts Flow cytometry of Galectin-4 staining with the polyclonal anti-galectin-4 antibody. Cells were treated as described in FIG. 3 except for using anti-galectin-4 polyclonal antibody, which was then detected by a fluorescent conjugated secondary molecule. The mouse anti-rabbit immunoglobulin (mIg-FITC) was used to detect the anti-galectin-4 rabbit polyclonal antibody. Panel (A) shows the anti galectin-4 binding to 2008 and 2008 C13*5.25 isotypes susceptible and resistant to cisplatin, respectively. Panel (B) shows the binding of anti galectin-4 to IGROV-1 and IGROV-1/CP isotypes susceptible and resistant to cisplatin, respectively. Panel (C) shows the binding of anti galectin-4 to A2780 and A2780/CP isotypes susceptible and resistant to cisplatin, respectively.

DETAILED DESCRIPTION

This invention relates to the field of diagnostics and therapeutics. In particular, this invention introduces molecules and methods that can be used to probe and predict the drug resistance in neoplastic and damaged cells, as well as detecting the cells that have potential to develop drug resistance. In addition, this invention introduces molecules and methods that can predict and assess the efficacy of the cytotoxic drugs in treating the diseased and damaged cells. Furthermore, the invention introduces a novel mechanism of cell internalization, namely "desialylation-mediated endocytosis", in which the cell surface desialylation triggers a series of reactions and induces transportation across the plasma membrane.

Resistance to cytotoxic agents is a common clinical problem in the treatment of neoplastic or damaged cells. "Multidrug resistant" and "multidrug resistance" (MDR) are used to refer to the development, in a neoplastic cell or damaged cell, of resistance to a number of different drugs that results in reduced efficacy of all the drugs concerned, including drugs to which the neoplastic cell or damaged cell was never exposed. MDR cells commonly exhibit a decrease in drug accumulation due to reduced uptake and increased efflux in resistant cells. Multi-drug resistant phenotype is shown to be associated with increased level of a series of specific cell membrane glycoproteins, namely p-glycoprotein and multidrug resistance-associated protein (MRP), [see Borst P., et al.: J. of Nat. Canc. Inst. (2000) 92:1295]. However, MDR is a multifunctional process in which many different types of structures are involved to make the resistant phenotype. This study has been focused on modification of the glycoconjugates in developing MDR.

Animal cell surfaces are essentially made of glycoconjugates that consist of glycolipids and glycoproteins. Glycans (sugar chains) linked to proteins and lipids of the plasma membrane create a meshwork that projects up to 100 Angstroms from the cell surface. This meshwork, known as glycocalyx, plays a defining role in cell membrane trafficking and cell-cell interactions [see Varki, A. et al., Essentials of glycobiology (1999). Cold Spring Harbor Laboratory, Cold Spring Harbor, N.Y.]. Recent studies have shown the association of glycans with drug resistance in cancer chemotherapy [see Nakahara, et al., Involvement of oligosaccharide changes in $\alpha 5\beta 1$ integrin in a cisplatin-resistant human squamous cell carcinoma cell line. Mol. Cancer Ther. (2003) 2:1207-14 and Liu, Y. et al, Ceramide glycosylation potentiates cellular multi-drug resistance. FASEB (2001) 15:719-30].

The majority of carbohydrates at the cell surface fall into three groups: those attached to lipids (glycolipids) and those attached to proteins, either through a nitrogen atom (N-glycans) or through an oxygen atom (O-glycans). Despite the overall complexity, mammalian glycans are composed of a limited set of monosaccharides that are building blocks of glycans in both glycolipids and glycoproteins. Combination of these units creates the diversity among the glycans. The most common monosaccharide units in mammalian glycans are hexoses and hexosamines such as glucose, galactose, mannose, N-acetylglucosamine-(GlcNAc), Nacetylgalactosamine (GalNAc) and fucose. In addition to hexose/hexosamine groups, the glycan structures also consist of another family of exclusive sugars known as sialic acids (Sia) or Neuraminic acids, from which the N-acetyl Neuraminic acid (5-NeuAc) is the most common form found in human tissues.

Sialic acids are a family of nine-carbon acidic sugars that typically terminate the glycan chains. The biosynthesis of glycans is well defined. The sugar chains attached to lipids or proteins always consist of a standard core structure specific to each group. Diversities come with the branches and extensions of the chains, yet, different glycans usually follow defined patterns in the outer gesture.

The sialic acids are typically found at the outermost ends of N-glycans, O-glycans and glycolipids. Terminal sialic acid can bind in linkages from carbon-2 (C-2) of sialic acid to either C-3 or C-6 of its underlying galactoside residue or C-8 of another sialic acid residue, to form the $\alpha 2$-3, $\alpha 2$-6 or $\alpha 2$-8 linkages. Thus, the underlying sugars are generally covered by sialic acids. Because of their terminal location and negative charge, sialic acids have unique capability to govern the glycan modifications, thus, interfere with the receptor-ligand bindings and result in regulation of cell signaling.

Sialic acids are the integral components of the cell membrane and more than 70% of the total cell contents of sialic acids are associated with plasma membrane. The sialylated glycosphingolipids (gangliosides), are the major constituents of the membrane glycolipid structures. Sugar chain elongation of gangliosides occurs in the Golgy and involves a series of gene-specific glycosyltransferase and translocase activities. Recent studies have revealed the translocase activity of the over-expressed multidrug resistant protein (MDR-1) in glycolipid biosynthesis in Golgy [see Lala P. et al, Retroviral Transfection of Madin-Darby Canine Kidney Cells with Human MDR1 Results in a Major Increase in Globotriaosylceramide and $10^5$- to $10^6$-Fold Increased Cell Sensitivity to Verocytotoxin; ROLE OF P-GLYCOPROTEIN IN GLYCOLIPID SYNTHESIS. J. Biol. Chem. (2000) 275, 6246-6251]. The MDR-1 translocase activity changes the balance between the non-sialylated and sialylated constituents of the glycolipid family in favor of non-sialylated molecules [see De Rosa M. F. et al, Role of multiple drug resistance protein 1 in neutral but not acidic glycosphingolipid biosynthesis. J. Biol. Chem. (2004) 279, 7867-76.]. The excess amounts of the non-sialylated glycolipids made in the over expressed MDR phenotype are transferred to the membrane [see Raggers R. J. et al, The human multidrug resistance protein MRP1 translocates sphingolipid analogs across the plasma membrane. J. Cell. Sci. (1999) 112:415-22]. Gangliosides have a hydrophobic tail group of ceramide (sphingosine and a long chain fatty acid) and a hydrophilic head group of two or more sugars (glucose and/or Galactose, sialic acid with or without N-acetyl galactosamine or N-acetyl glucosamine). The gangliosides' head group oligosaccharide chain extends up to 2.5 nm from the membrane/water interface (Ravindranath M. H., Immunology of gangliosides. Indi. J. Expe. Biol. (2000) 38:301-12). Thus, the terminal sialic acids, are the most exposed molecules to encounter the extra cellular signals, and this exposure needs to be carefully regulated.

The sialic acid masking, a well documented phenomenon in sialic acid biology, is a control mechanism in glycan-mediated interactions [see Schauer R., Sialic acids and their role as biological masks. Trends Biochem. Sci. (1985) 10:357]. Masking and unmasking of sialic acids interfere with different receptor—ligand interactions [see Pilatte Y., Sialic acids as important molecules in the regulation of the immune system: pathophysiological implications of sialidases in immunity. Glycobiology (1993) 3:201]. Desialylation uncovers the underlying galactoside residues and allows binding of the galactoside-binding proteins to desialylated glycans. Such bindings can induce signals in diverse biological phenomena that entirely alter the cell fate (e.g. from death to survival). A defined family of mammalian lectins that bind galactoside residues and can be involved in membrane signaling are Galectins.

Galectins are a category of conserved beta galactoside-binding lectins that are synthesized in the cytoplasm but also reach the cell surface by a poorly understood process in which they become enclosed in membrane vesicles that fuse with the plasma membrane [see Hughes, R. C. Secretion of the galectin family of mammalian carbohydrate-binding proteins. Biochem. Biophys. Acta. (1999)1:172-85]. With respect to the characteristic features of Galectins in their ligand binding capacity and membrane trafficking we consider Galectins as candidates for membrane transporters, which may as well be involved in drug delivery.

In the present studies, a panel of isogenic pairs of the human ovarian carcinoma cell lines, sensitive and resistant to a series of cytotoxic drugs, was profiled for their cell surface glycans and galectins. The comparison of the glycan profiles of sensitive and resistant cells demonstrates the cell surface glycan modifications in MDR developments. The most profound difference in the cell surface glycans of the sensitive and resistant cells appears in the contents of the cell surface α2-6 linked sialic acids. A clear decrease in binding of cells to SNA, a specific lectin to α2-6 linked sialic acids, was documented in MDR cells compare to the SNA binding to the sensitive isotypes. This observation declares that the decrease in the contents of α2-6 sialic acids is associated with multi-drug resistant phenotype in neoplastic and damaged cells. The finding disclose the first invention in this work that: the α2-6 linked sialic acids and its level of appearance at the cell surface can be used as a marker to probe, predict and assess the efficacy of the drugs to be used in chemotherapy of neoplastic diseases and the damaged cells. This finding will be helpful in therapeutic managements and in developing appropriate strategies for chemotherapy.

Furthermore, the in-forced desialylation, by using the exogenous sialidase along with the drug, facilitates the drug uptake and partially restores the cell sensitivity to the drugs in resistant phenotypes. These findings outline the second invention (discovery) in the present work and introduce the "desialylation-mediated endocytosis" as a novel mechanism in cell trafficking. With respect to this functionality, sialic acid manipulation, such as sialylation/desialylation or masking/unmasking of sialic acids, can launch a powerful therapeutic strategy. Therefore, the present discoveries have broad applications in therapeutics and diagnostics.

Observations that Form the Basis of the Invention

The three isotype pairs of the ovarian carcinoma cell lines, 2008 and 2008/C13* 5.25, IGROV-1 and IGROV-1/CP, A2780 and A2780/CP, each pair consists of parental sensitive cell line and its corresponding MDR phenotype, respectively, were used in these studies. Dichlorodiaminocisplatin (DDP) was selected as a sample drug to conduct the experiments. The studies were performed by three different techniques of:
1—Fluorescent deconvoluting microscopy
2—Cytotoxicity assay measured by colony-forming ability
3—Fluorescent Activated Cell Sorting (FACS)

Fluorescein-labeled DDP (F-DDP) was used in digital deconvoluting microscopy technique to assess the general distribution of the drug in sensitive and MDR cells. The effects of F-DDP, compare to DDP, has been validated and this compound has been utilized in studies of sub-cellular localization of cisplatin in susceptible and resistant cells [see Safaei R, et al: Intracellular localization and trafficking of fluorescein-labeled cisplatin in human ovarian carcinoma cells. Clin. Cancer Res. (2005) 11, 756-67

FIG. 1 depicts the association of F-DDP with the cell membrane in 2008/C13*5.25 resistant isotype. The green fluorescent (F-DDP) is associated with the cell membrane. The accumulation of F-DDP at the cell surface is confirmed by strong yellow color at the cell membrane generated by merging the red staining of the cell surface actin (Alexa Flour 647 phalloidin) with F-DDP (green fluorescein). FIG. 1 shows the F-DDP distribution after one hour incubation with the drug in resistant cells, it is noteworthy that in sensitive cells by 2-5 minutes fluorescence (F-DDP) disappeared from the cell membrane and was observed in association with cytoplasmic organelles [see Safaei R, et al: Intracellular localization and trafficking of fluorescein-labeled cisplatin in human ovarian carcinoma cells. Clin. Cancer Res. (2005) 11, 756-67]. This result, thus, indicates a decrease in the uptake and an increase in accumulation of the drug at the cell surface in resistant phenotype.

To examine the role of glycosylation on drug resistance, the resistant cells were treated with Arthrobacter ureafaciens sialidase (AUS), a bacterial enzyme that removes the terminal sialic acids from the cell surface glycans, concomitant with cisplatin treatment. The sialidase/cisplatin treatment encouraged the cisplatin internalization and increased the sensitivity of the cells, thus, it almost overcame the resistance at this experiment (shown in FIG. 2 and cytotoxicity assay). FIG. 2 demonstrates the disappearance of F-DDP from the cell surface when the F-DDP treatment was performed in the presence of sialidase. The results imply that desialylation facilitates the drug uptake and induces the endocytosis. To confirm the internalization of the drug by sialidase treatment, the result was further confirmed by clonogenic assay (see below).

To confirm the sialidase effects on F-DDP internalization and sensitizing the resistant cells to the drug, the resistant cells were tested in cytotoxicity assay to determine colony formation ability with cisplatin treatments in the presence and absence of sialidase. Resistant cells were treated with high concentration of cisplatin (25 µM, an IC-50 about 10 fold higher than that of the sensitive cells) in the absence and presence of 5 mU sialidase (see table 1 in "Experimental procedures"). The colony formation ability of MDR cells was reduced 40-50%, when sialidase concomitant with cisplatin was added to the resistant cells compare to the resistant cells treated with the same amounts of cisplatin in the absence of sialidase. The data, thus, support the sialidase-mediated drug internalization and increasing the cytotoxicity of the drug.

To profile the contents of the cell surface glycans on susceptible and resistant phenotypes a panel of fluorescently conjugated (FITC) plant lectins, specific to different carbohydrate units, were used in the Fluorescent Activated Cell Sorting (FACS).

Figure 1A:
Figure 1B:
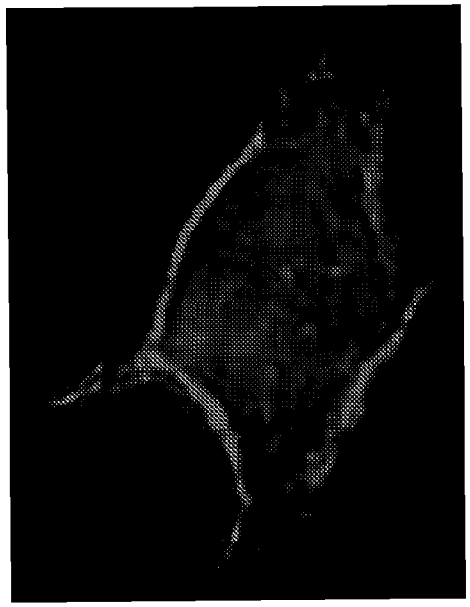
Figure 1C:
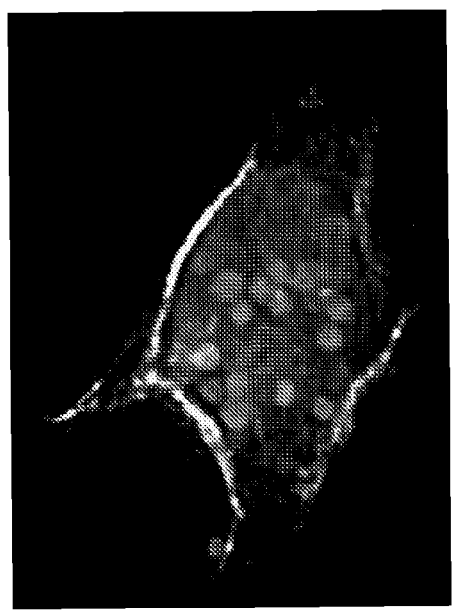
Figure 1D:
Figure 2B:
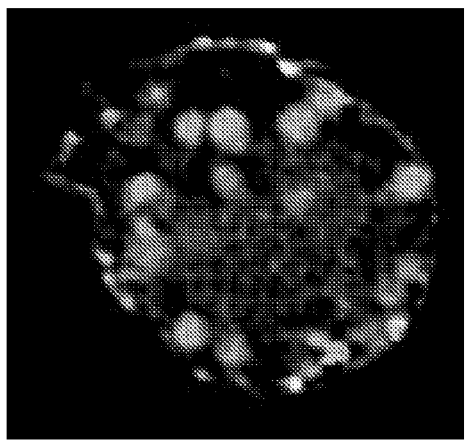
Figure 2D:
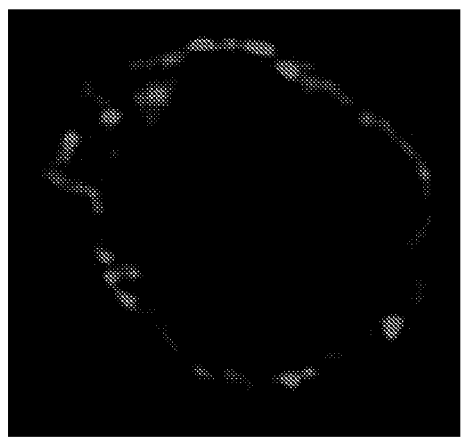
Figure 2A:
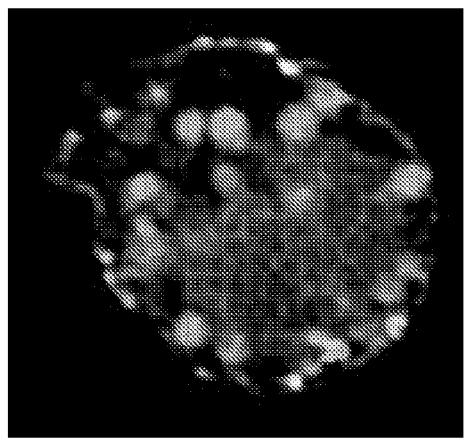
Figure 2C:
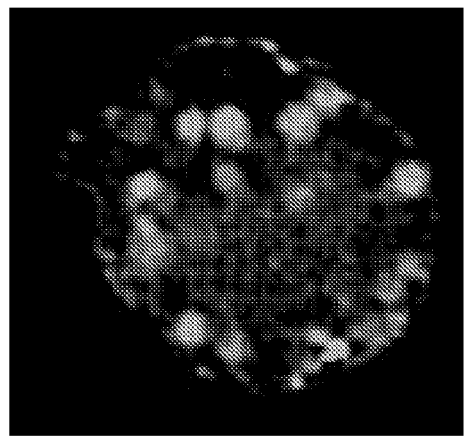
Figure 3A:
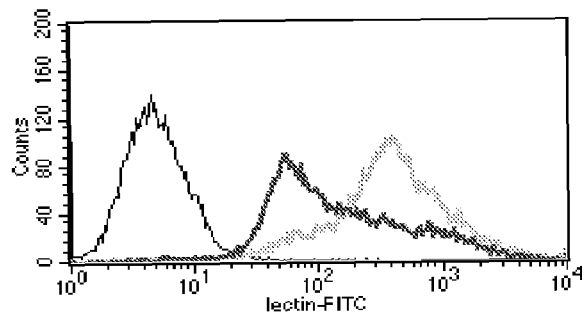
Figure 3B:
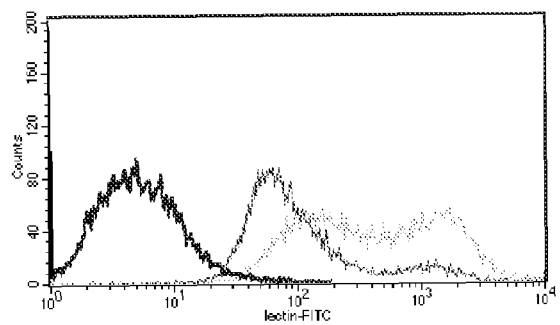
Figure 3C:
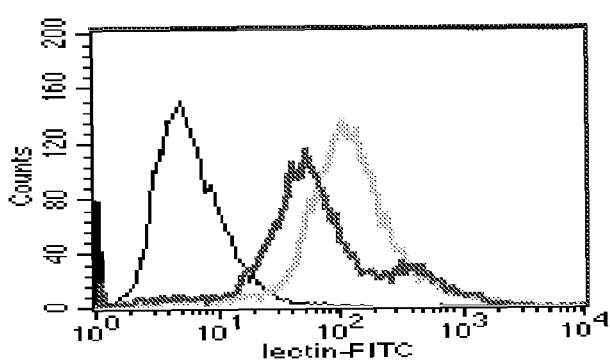

The fluorecein-labeled Sambucus Nigra (FITC-SNA), a plant lectin that specifically binds to the terminal α2-6 linked sialic acid, was used in all three isogenic pairs of 2008 and 2008/C13* 5.25, IGROV-1 and IGROV-1/CP, A2780 and A2780/CP, to detect the available cell surface sites of α2-6 linked sialic acids. As shown in FIG. 3, a significant decrease in SNA binding to α2,6 linked sialic acids in all three cell pairs were observed in resistant cells relative to their sensitive counterparts. This decrease in SNA binding could be attributed to either the lower contents of the α2-6 sialic acid sites [see De Rosa M. F. et al: Role of multiple drug resistance protein 1 in neutral but not acidic glycosphingolipid biosynthesis. J. Biol. Chem.: (2004) 279, 7867-76.] and to masking of the sialic acid sites by other cell surface modifications [see Cumber, P. M. et al: Increased Drug Accumulation ex Vivo with Cyclosporin in Chronic Lympatic Leukemia and Its Relationship to Epitope Masking of P-Glycoprotein. LEUKEMIA (1991) 5, 1050-53].

FIG. 3 clearly demonstrates a decrease in SNA binding to α2-6 sialic acids in resistant phenotypes. To test whether the changes in the cell surface sialic acids extend to other types of sialic acid linkages, the contents of Sialic acids with α2,3 linkage was also tested and compared in susceptible and resistant cells. Binding of three cell pairs to FITC-Maackia amurensis (FITC-MAA), a plant lectin specific to Sia α2,3, was tested by FACS analysis. As shown in FIG. 4, the cell surface contents of Sia α2,3 was unchanged in sensitive and resistant phenotypes (FIG. 4). Therefore the decrease in the amounts of the cell surface sialic acid was specific to Sia α2,6 Gal/GalNAc.

The lower contents of the Sia α2,6 in resistant cells could be interpreted in three ways; 1—It could just be limited to the absence of the terminal sialic acid, (possibly due to a defect in sialyltransferase (ST6 Gal/GalNAc) activities; 2—it may reflect the absence or defects of glycan chains on their protein or lipid scaffold (changes in glycan structures in glycoolipids and O-glycoproteins have been reported in MDR phenotypes). 3—it could also reflects the missing of some glycoproteins and/or glycolipids components of the cell membrane.

The first possibility, i.e. the absence of terminal Sia α2,6, can be verified by assessing the contents of its underlying sugars. The underlying sugars to Sia α2,6 are mainly N-acetyllactosamine (Galβ1,4GlcNAc, i.e. LacNAc) and N-acetylgalactosamine (GalNAc). These structures can be tested by two plant lectins namely Erythrina cristagalli (ECA), that binds to LacNAc/GalNAc and Peanut agglutinin (PNA), that binds to Galβ1,3GalNAc. Both lectins were tested in the present studies.

FITC-ECA was tested in FACS analysis to evaluate the contents of LacNAc. As shown in FIG. 5, all three cell pairs demonstrated strong binding to ECA suggesting a high contents of LacNAC/GalNAc on these cells. The intense fluorescent, due to high contents of the ligands, caused technical problems in some of the samples that made the comparison of susceptible and resistant cells very difficult. Nonetheless, general increase in the contents of LacNAc/GalNAc was concluded for resistant cells that was consistent with a decrease in terminal Sia α2,6 (i.e. revealing the underlying sugar) in resistant phenotypes.

On the other hand, the cell binding to FITC-PNA, a lectin specific to Galβ1,3GalNAc and to a lesser extend to lactose, showed a decrease in the amounts of Galβ1,3GalNAc in resistant cells (FIG. 6). Galβ3GalNac is mainly found in "core 1" of the o-linked glycans, as well as the ganglioside types of GM1, GD1 and GT1 that are multi-sialylated members of the ganglioside family and common structures of the lipid rafts in plasma membrane. Decrease in both Sia α2,6 and Galβ1,3GalNAc strongly suggest major remodeling of gangliosides and the O-linked glycans. Galβ1,3(Sia α2,6) GalNAc and Sia α2,6GalNAc, known as sialyl T and Sialyl Tn antigens, respectively, are reported to be associated with cancer development.

With respect to a possible role for Galectin-mediated membrane trafficking in drug delivery, the three cell pairs of susceptible/resistant cells were also tested in FACS analysis with the polyclonal rabbit antibodies against human galectin-1 and galectin-4. FITC mouse anti-rabbit Ig was used as a secondary antibody to detect the signals. Despite the fact that galectins are not membrane-bound and their presence and stability on the cell surface depends on their association with carbohydrate ligands, these cells showed high contents of galectins at the cell surface of both susceptible and resistant phenotypes (FIGS. 7 and 8). Apparently binding of galectins to the galactoside cell surface ligands was strong enough to stand the washing process involved in cell suspension in the cell sorting assay (FACS analysis). Therefore, the high contents of Galectin-1 and 4 were demonstrated on susceptible and resistant cell surfaces, however, a cautious conclusion may estimate a lower amounts of Galectins on the resistant cells.

EXPERIMENTAL PROCEDURES

1—Tissue Culture Model

Three isogenic pairs of sensitive and multidrug resistant phenotypes of human ovarian carcinoma cell lines were studied. The resistant cells were developed by chronical exposure of the parental cell lines, 2008, A2780, IGROV-1 to progressively increased concentration of cisplatin to obtain the corresponding resistant phenotypes of 2008/C13*5.25, A2780/CP and IGROV-1/CP, respectively. The resistant sub-lines showed 10.4, 6.9 and 7.6 fold increase in IC-50 to cisplatin resistance for 2008/C13*5.25, A2780/CP and IGROV-1/CP respectively. The resistant phenotypes also showed different degrees of cross-resistance to different cytotoxic drugs in used in chemotherapies. The morphology of the resistant cells differed from the sensitive isotypes, consistent with the cell surface molecular modifications.

Cells were maintained in RPMI 1640 medium with 10% fetal bovine serum in humidified air with 5% CO2. Histochemistry was performed on cells one day after seeding them on coverslips. Labeling with 2 μM F-DDP was performed in OPTIMEM at 37° C. for 1 h.

2—Fluorescent Microscopy

A fluorescently labeled cis-platin. Fluorescent Diamino Dichloro Platin (F-DDP) capable of forming cross-links via platinum moiety with subcellular compartments was used in deconvoluting microscopy. The F-DDP was made according to [Molenaar C, et al. New insights in the cellular processing of platinum antitumor compounds, using fluorophore-labeled platinum complexes and digital fluorescence microscopy. J Biol Inorg Chem (2000) 5:655-65]. F-DDP can also be cross-linked with formaldehyde to proteins via the fluorescein tag. Images were captured from 0.2 m sections by 100× and 40× lenses and SoftWorx software (Applied Precision, Inc) was used for deconvoluting data. F-DDP distribution in cells was distinct from that of the controlled tagged of carboxyfluorescein and was shown to be markedly different in multiple isogenic pairs of DDP-sensitive and resistant ovarian carcinoma cells. In DDP-sensitive cells, F-DDP accumulates within the cytoplasm. In contrast, in DDP-resistant cells the plasma membrane or immediate sub-membrane region was the primary site of F-DDP accumulation (FIG. 1).

3—Cytotoxicity Assay by Colony Forming Ability

Colony forming ability assay was performed by seeding 100 cells/ml of sensitive or resistant isotypes per each well/ml in 12 well plates. Cells were cultured with DMEM, 10% FBS overnight. The assay was performed in 4 plates for each of the sensitive or resistant isotypes in the format shown in Table 1 and was repeated three times. 2008 isotype pair were used in the experiment. Sensitive cells could not tolerate such high concentration of cisplatin, used in the assay, to serve the resistant cells, as the IC-50 was 10 fold higher for resistant cells compare to their parental susceptible phenotype.

TABLE 1

The plate format for cytotoxicity assay.

| Plate No. | −pt/ −sialidase | +pt/ −sialidase | +pt/ +sialidase | −pt/ +sialidase |
|---|---|---|---|---|
| 1 | + | − | − | − |
| 2 | | + | − | − |
| 3 | | − | + | − |
| 4 | | | | + |

Table 1: Colony forming ability was performed by seeding 100 cells/ml of sensitive or resistant isotypes per each well/ml in 12 well plates. Cells were cultured with DMEM, 10% FBS overnight. The assay was performed in 4 plates for each of the sensitive or resistant isotypes in the above format and was repeated three times for each cell pair. plate 1 (control): DMEM, 10%FBS; plate 2: DMEM containing 25 μM cisplatin; plate 3: DMEM containing 25 μM cisplatin and 5 mU neuraminidase (AUS); plate 4: DMEM containing 5 mU neuraminidase.

After one hour incubation at 37 degree C., 5% $CO_2$, the media of different treatments were removed from the wells. Cells were then washed with DMEM and was replaced by fresh DMEM, 10% FBS. Incubation continued for about two more weeks for the colonies to appear.

The concentration of cisplatin was too high for the sensitive cells to tolerate the drug, therefore almost no real colony formed in any of the sensitive cultures except for the plate #1 (no treatment). For resistant cells, the plate #1, the control cells were confluent by the end of two weeks. This plate was considered as 100% growth. In plate #2 (cisplatin treatment), the cell growth was about 80% of the control. In plate #3, (concomitant treatment of ciaplatin/sialidase) colony formation was reduced to about 30% of the control, i.e. less than 50% colony formation was observed compare to the plate #2 that was treated with cisplatin, in plate #4, (treated with sialidase), cells were about confluent by the end of two weeks.

Fluorescent Activated Cell Sorting (FACS) Analysis:

Flow cytometry was performed on a Becton Dickinson FACscan machine. Ovarian carcinoma cell lines 2008, A2780 and IGROV-1, sensitive to cisplatin, and their resistant corresponding sublines, 2008/C13*5.25, A2780/CP and IGROV-1/CP were detached from plates by mild trypsinization. After washing three times with ice-cold PBS containing 0.02% Na-Azide, all cell types were incubated in the same buffer with fluorescently labeled lectins for one hour. A panel of fluorescently labeled lectins (FITC-lectins) specific to different glycans were used in FACS analysis to compare the carbohydrate profiles on susceptible and resistant cell membranes. The tested lectins were as follows: Fluorecin conjugated Sambucus nigra (FITC-SNA), a lectin that binds to sialic acid with α2,6 linkage to underlying Gal or GalNAc (Siaα2,6Gal/GalNAc). FITC-Maackia amurensis (FITC-MAA), a plant lectin specific to Sia α2,3 linkages, FITC-Peanut Aglutinin (FITC-PNA), a lectin specific to Galβ1, 3GalNAc and to a lesser extend to lactose, FITC-Erythrina Cristagalli (FITC-ECA), that binds to N-Acetyllactosamine (LacNAc) and N-Acetylgalactosamine (GalNAc), LacNAc/GalNAc. The presence of galectin 1 and galectin 4 on the cell surface of all sensitive cell lines and their resistant sublines were tested using polyclonal rabbit antibodies against human galectin-1 and human galectin-4. These antibodies were then detected by FACS analysis with mice FITC-Ig against rabbit immunoglobulin.

Different Aspects of the Invention

Generally speaking, the invention relates to Sialic acids and related molecules in developing diagnostics and therapeutics methods for multidrug resistance. The results also discover a novel mechanism in cell trafficking that is called: "Desialylation; a novel trigger for endocytosis". The present invention stems from the realization that: 1) The cell surface content of sialic acids is associated with susceptibility and resistance phenotypes in neoplastic and damaged cells, 2) The difference in the contents of the cell surface sialic acid in resistant cells compare to their sensitive counterparts is more pronounced in sialic acids with α2-6 linkages, 3) A general decrease in the amounts of the α2-6 linked sialic acid is present in resistant phenotype compare to its corresponding sensitive parental cells, 4) Treating the resistant phenotype with neuraminidase, an enzyme that removes the sialic acid from the sugar chain, facilitates the drug internalization and reinstalls the cell susceptibility to the drug, 5) The present data, introduce a novel mechanism of endocytosis that is mediated by "desialylation" on the cell surface. 6) Desialylation initiates a series of reactions that lead to the compound delivery across the membrane. "Desialylation-mediated endocytosis" is a novel concept in membrane trafficking and compound delivery that has never been discovered in the prior art.

These findings identify the cell surface α2-6 sialic acids and sialic acid-related structures (i.e. glycolipids, glycoproteins and glycan binding molecules) as "biomarkers" that can probe, predict and assess the efficacy of therapeutic drugs in neoplastic diseases or damaged cells. Methods of detecting the sialic acid related markers are introduce as follows: sialic acids can be simply detected by variety of available binding molecules that are labeled and can bind to sialic acids. The sialic acid binding molecules could be obtained from different origins of mono-or multi cellular organisms, such as: viral, bacterial, plant and animal substances. These compounds can be proteins, lectins, antibodies, lipids and glycans specific to sialic acids with different binding features. "Desialylation" can be prevented or promoted, by different chemical and biological methods to increase cytotoxicity. "Desialylation" can be promoted by using sialidases, chemical and biological reactions to stimulate sialic acids and/or change the cell membrane structures and enforce endocytosis to increase cytotoxcity. Sialic acid analogs can be used to induce the desialylation-mediated endocytosis mechanism. Various aspects of the invention may include:

1. A method for detecting multidrug resistance or multidrug resistance potential in a test neoplastic cell comprising: a) measuring a level of cell surface content of α2-6 linked sialic acid, and/or any sialic acid related molecule, in the test neoplastic cell of a given origin or cell type, and b) comparing the level of cell surface-content of α2-6 linked sialic acids, and/or any sialic acid related molecule, in the test neoplastic cell to the level of cell surface content of α2-6 linked sialic acids in a non-resistant neoplastic cell of the same origin or cell type, wherein the test neoplastic cell is multidrug resistant or has multidrug resistance potential if the level of cell surface-contents of α2-6 sialic acids, or sialic acid related molecule, in the test neoplastic cell is lower than the level of cell surface content of α2-6 linked sialic acids, or sialic acid related molecule, in the nonresistant. neoplastic cell of the same given origin or cell type.

2. The method of claim 1, wherein measuring the level of cell surface sialic acids in the test neoplastic cell comprises contacting said cell with a sialic acid-binding agent and measuring the level of sialic acid binding agent bound to cell surface sialic acids.

3. The method of claim 2, wherein the sialic acid binding agent is selected from the group consisting of natural ligands, synthetic small molecules, chemicals, nucleic acids, peptides, proteins, lectins and antibodies.

4. The method of claim 2 and 3, wherein the sialic acid-binding agent is selected from the chemical source or any natural source such as mono-cellular, multi-cellular, microbial, bacterial, viral, plants and animals.

5. The method of claim 2 and 3 and 4, wherein the sialic acid-binding agent is labeled with a group consisting of fluorophore, chemical dyes, radioactive compounds, chemoluminescent compounds, magnetic compounds, paramagnetic compounds, promagnetic compounds, enzymes that yield a colored product, enzymes that yield a chemoluminescent product, and enzymes that yield a magnetic product.

6. The method of claim 1, wherein the test neoplastic cells is selected from the group consisting of a promyleocytic leukemia cell, a T lymphoblastoid cell, a breast epithelial cell, an ovarian cell and a head and neck carcinoma cell.

7. The method of claim 1, wherein the test neoplastic cell is selected from a group consisting of a lymphomacell, a melanoma cell, a sarcoma cell, a leukemia cell, a retinoblastoma cell, a myeloma cell, a glioma cell, a mesothelioma cell, and a carcinoma cell.

8. A method for detecting a multidrug resistant cell in a patient comprising: (a) administering to the patient, a sialic acid binding agent operably linked to a detectable label; and b) detecting the label operably linked to the sialic acid binding agent, wherein the sialic acid binding agent specifically binds to cell surface sialic acids on a multidrug resistant cell in patient.

9. The method of claim 8, wherein the patient is a human and suffering from a disease or disorder caused by the presence of the multidrug resistant cell.

10. The content of the cell surface sialic acids is involved in cell susceptibility and resistance to therapeutic agents.

11. The cell surface sialic acids are involved in endocytosis and membrane trafficking.

12. A decrease in the contents of sialic acid $\alpha$2-6 linkages on the surface of multidrug resistant phenotypes compare to the contents of $\alpha$2-6 linked sialic acid in susceptible cells is a marker to predict the efficacy of cytotoxic drugs in chemotherapy of the neoplastic and damaged cells.

13. The contents of the cell surface sialic acids represent plasma membrane remodeling due to glycolipids and glycoproteins modifications.

14. The contents of the cell surface sialic acids represent changes in the cell surface glycolipids, such as glycosphingolipids and gangliosides, possibly, as a result of the multi drug resistant (MDR) enzyme activity that is involved in translocation of glucosylceramides in the Golgy apparatus.

15. Methods of using gangliosides to probe, predict and assess the multi drug resistance in the diseased cells.

16. Methods of testing the sialic acid related masking/unmasking of the effector sites involved in signal transduction and cell membrane trafficking.

17. Methods of using sialic acids as marker to predict the drug susceptibility/resistance in chemotherapy with different types of therapeutic drugs.

18. Methods of using sialic acids in $\alpha$2-6 linkages as marker to predict the likelihood of resistance to chemotherapy with different types of therapeutic drugs.

19. Methods of using sialic acid related molecules such as its underlying glycans or sialic acid binding molecules to predict the likelihood of resistance to chemotherapy with different types of therapeutic drugs.

20. Methods of using "Desialylation" of the cell surface glycoconjugates to trigger a general mechanism of endocytosis.

21. Methods of using "Desialylation" to induce a mechanism of endocytosis that facilitates the drug delivery into the cells.

22. Methods of using the contents of any Galectins family members in the cells or on the cell surface to predict the drug resistance to chemotherapy.

23. Method that demonstrates "Desialylation" can initiate a signal transduction mechanism that determines the cell fate (apoptosis or survival), depending on the effector molecules that are involved and stimulated.

24. Methods of using of sialic acids as a marker for probing or assessing the therapeutic efficacy of anti-neoplastic drugs in malignancy.

25. Methods of using of sialic acids as a marker for probing or assessing the therapeutic efficacy of antibacterial and antiviral drugs 26. Methods of using of sialic acids as a marker for probing or assessing the therapeutic efficacy of immunosuppressant or immune-activating drugs 27. Methods of using of sialic acids as a marker for probing or assessing the therapeutic efficacy of anti-inflammatory drugs.

28. Methods of using of any luminescent-tagged, fluorescent-tagged or other tagged molecules, that are detectable in the laboratory techniques of histology, biochemistry, cell culture and molecular biology to detect the sialic acid and assess sialic acid contents (from 0-100 percent) of the cells or tissues to probe, predict and estimate the drug susceptibility or resistance of malignant cells.

29. Methods of using of any plant lectins, animal antibodies and sialic acid binding molecules, such as Siglecs, to detect the contents of sialic acids on the cells or tissue sections to predict the susceptibility/resistance to the drug. The sample lectins are: Sambucus Nigra Agglutinin (SNA), and/or Maackia amurensis Leukoagglutinin (MAL), and/or Limax flavvs (LFA) and or any mammalian sialic acid binding lectins that are known as "Siglecs"—Sialic acid binding Immunoglobulin type Lectins.

30. The method of claim 29, wherein the lectins are labeled with any kind of chemiluminescent, fluorescent tagged or radio labeled agent to be used in histological, biochemical, cell culture and molecular biology techniques.

31. Methods of using of Galactosides and/or Galactosaminosides to assess their contents (from 0-100 percent) of the cells or tissues to probe, predict and estimate the drug susceptibility or resistance of the diseased cells.

32. The method of claim 31, wherein the molecule to be used is Plant lectin samples such as Peanuts agglutinin (PNA), Phaseolus vulgaris Leukoagglutinin (L-PHA), Phaseolus vulgaris Erythroagglutinin (E-PHA), 33. The method of claim 31, wherein the molecule to be used is animal galactoside binding compound, such as animal lectins and antibody against galactosides.

34. The method of claim 31, wherein the molecules in use are labeled with any kind of chemiluminescent, fluorescent tagged or radio labeled agent to be used in histological, biochemical, cell culture and molecular biology techniques.
35. Methods of using of any chemiluminescent-tagged, fluorescent-tagged or any radio-labeled molecules, that are detectable in the laboratory techniques of histology, biochemistry, cell culture and molecular biology to detect any kind of glycolipids and assess the contents of these molecules in or on the cells or tissues.
36. Methods of using of any lectins that detect the carbohydrate moiety of glycolipids and glycoproteins in any kind of chemiluminescent/fluorescent tagged in histological, biochemical, spectroscopy and cell culture techniques.
37. Methods of using of any kind of carbohydrate precursor molecules to label and chase the glycan biosynthesis involved in cell susceptibility and resistance.
38. Methods of using of any molecules such as: Glucosides, Galactosides, fucosides, sialosides and their derivatives of acetylated, sulfated, phosphorylated that are non-tagged or chemoluminescent-tagged, fluorescent-tagged, radio-labeled, amino and/or azido labeled and/or attached to spacer molecules that can be used to inhibit or stimulate glycan-associated susceptibility/resistance reactions.
39. Methods of using of any protein, antibody or any amino acid-based compounds that are non-tagged or radio labeled, chemiluminescent-tagged, fluorescent-tagged, amino acid tagged and azido tagged and/or attached to any spacer molecules that bind carbohydrate moiety of glycoproteins, such as Glucosides, Galactosides, Fucosides, Sialosides and their derivatives of acetylated, sulfated, phosphorylated, to detect glycan presence and assess their contents in the cells or on the cell surface in relation to drug susceptibility and resistance.
40. Methods of using of any protein, antibody, or any amino acid-based compounds that are non-tagged or chemiluminescent-tagged, fluorescent-tagged, amino acid tagged, radio-labeled and azido tagged and/or attached to any spacer molecules that bind carbohydrate moieties of proteoglycans, such as Glucosides, N-acetylglucosides, Galactosides, N-acetylgalactosides, Fucosides, Xylosides, Sialosides, Uronic acids, Iduronic acids, Glucoronic acids and/or their derivatives of acetylated, sulfated, phosphorylated, to detect glycan presence and assess their contents in the cells or on the cell surface in relation to drug susceptibility and resistance
41. Methods of using of antibodies or any amino acid-based compounds that are non-tagged or chemoluminescent-tagged, fluorescent-tagged, amino acid tagged and azido tagged and/or attached to any spacer molecules that bind carbohydrate moiety of glycolipids containing any of the sugar units, such as Glucosides, Galactosides, Fucosides, Sialosides and their derivatives of acetylated, sulfated, phosphorylated, or combination of the sugar units that form glycolipid antigens, to detect the glycan presence and assess their contents in the cells or on the cell surface.
42. Methods of using of galactosides or any carbohydrate-based compounds specific to galectin-binding within the cells or on the cell surface to detect galectins and to estimate and/or predict the resistance to metal-binding drugs.
43. Methods of using of combinations of lectins or other proteins to assess contents of the sialic acids and/or galactosides and/or any amino acid-based or carbohydrate-based compounds that detect Galectins to predict the likelihood of drug resistance.
44. Methods of using of galectins or galectin-mediated compounds, such as galectin activators or inhibitors to exert galectin-mediated mechanism to break the resistance of the cells to any cytotoxic drugs.
45. Methods of using of exogenous sialidases such as any kind of microbial, plants or animal neuraminidases to overcome the resistance of the cells to cytotoxic drugs.
46. Methods of using of any kind of chemical or biological synthetically made or naturally extracted compounds to stimulate either desialylation or sialic acid modifications to induce sialic acid-mediated drug internalization.
47. Methods of using of any kind of chemical or natural compounds to stimulate either desialylation or sialic acid modifications to increase sensitivity of the cells to the drug and breaking the resistance.
48. Methods of using of any enzymatic procedure or chemical methods that can introduce sialic acids to the cells to modify the cell structure and induce cytotoxicity or breaking the resistance.
49. Methods of using any chemical and/or biological method that synthesize sialic acids and its analogues to modify the glycan structures to induce cytotoxicity or breaking the resistance.
50. Methods of using of any chemical or biological molecule that can mask sialic acids and prevent their effects on drug delivery and induce drug resistance
51. Methods of using of any carbohydrate analogue agonist or antagonist to sialic acids that can induce drug sensitivity or breach the resistance to the drug.
52. Methods of using any molecule that can probe the contents of glycolipids as a marker for drug resistant
53. Methods of using any protein or antibody to detect the contents of glycolipids in prediction of resistance, in diagnostic and therapeutic purposes.

The invention claimed is:
1. A method of determining whether neoplastic cells from a cancer patient are likely to be multiple drug resistant (MDR) neoplastic cells, said method comprising:
obtaining a sample of candidate MDR neoplastic cells from said cancer patient;
determining the amount of α 2-6 linked sialic acid bound to the surface of said candidate MDR neoplastic cells; and
comparing the amount of α 2-6 linked sialic acid bound to the surface of said candidate MDR neoplastic cells to the amount of α 2-6 linked sialic acid bound to the surface of cells that have been determined to be drug sensitive neoplastic cells of the same cell type as said candidate MDR neoplastic cells, wherein a decreased amount of α 2-6 linked sialic acid bound to the surface of said candidate MDR neoplastic cells as compared to the amount of α 2-6 linked sialic acid bound to the surface of said drug sensitive neoplastic cells indicates that the candidate MDR neoplastic cells are likely to be MDR neoplastic cells.
2. The method of claim 1, wherein determining the amount of said α 2-6 linked sialic acid bound to the surface of said candidate MDR neoplastic cells comprises measuring the amount of a sialic acid binding agent bound to said α 2-6 linked sialic acid.
3. The method of claim 2, wherein said sialic acid binding agent is selected from the group consisting of lectins and antibodies.
4. The method of claim 2, wherein said sialic acid binding agent comprises a label.

5. The method of claim 4, wherein said label is selected from the group consisting of a fluorescent label, a chemiluminescent label, a radioactive label, a magnetic label, a paramagnetic label, a promagnetic label and a colorometric label.

6. The method of claim 2, wherein said sialic acid binding agent is *Sambucus nigra* agglutinin (SNA).

7. The method of claim 1, wherein said candidate MDR neoplastic cells are selected from the group consisting of lymphoma cells, melanoma cells, sarcoma cells, leukemia cells, retinoblastoma cells, myeloma cells, glioma cells, mesothelioma cells and carcinoma cells.

8. A method of determining whether neoplastic cells from a cancerous tissue of a cancer patient are likely to be multiple drug resistant (MDR) cancer cells, said method comprising:
   obtaining a first sample of neoplastic cells from a cancerous tissue from said cancer patient;
   determining the amount of α 2-6 linked sialic acid bound to the surface of said first sample of neoplastic cells;
   obtaining a second sample of neoplastic cells from said cancerous tissue after said patient has been treated with a chemotherapeutic agent for the treatment of cancer;
   determining the amount of α 2-6 linked sialic acid bound to the surface of said second sample of neoplastic cells; and
   comparing the amount of α 2-6 linked sialic acid bound to the surface of said first sample of neoplastic cells to the amount of α 2-6 linked sialic acid bound to the surface of said second sample of neoplastic cells, wherein a decreased amount of α 2-6 linked sialic acid bound to the surface of said second sample of neoplastic cells as compared to the amount of α 2-6 linked sialic acid bound to the surface of said first sample of neoplastic cells indicates that the neoplastic cells of said cancerous tissue are likely to be MDR neoplastic cells.

9. The method of claim 8, wherein determining the amount of said α 2-6 linked sialic acid bound to the surface of said first sample of neoplastic cells comprises measuring the amount of a sialic acid binding agent bound to said α 2-6 linked sialic acid.

10. The method of claim 9, wherein said sialic acid binding agent is selected from the group consisting of lectins and antibodies.

11. The method of claim 9, wherein said sialic acid binding agent comprises a label.

12. The method of claim 11, wherein said label is selected from the group consisting of a fluorescent label, a chemiluminescent label, a radioactive label, a magnetic label, a paramagnetic label, a promagnetic label and a colorometric label.

13. The method of claim 9, wherein said sialic acid binding agent is *Sambucus nigra* agglutinin (SNA).

14. The method of claim 8, wherein said cancerous tissue comprises neoplastic cells selected from the group consisting of lymphoma cells, melanoma cells, sarcoma cells, leukemia cells, retinoblastoma cells, myeloma cells, glioma cells, mesothelioma cells and carcinoma cells.

15. A method of determining whether a neoplastic cell is likely to be a multiple drug resistant (MDR) neoplastic cell, said method comprising:
   obtaining a candidate MDR neoplastic cell;
   determining the amount of α 2-6 linked sialic acid bound to the surface of said candidate MDR neoplastic cell;
   comparing the amount of α 2-6 linked sialic acid bound to the cell surface of said candidate MDR neoplastic cell to the amount of α 2-6 linked sialic acid known to be bound to the cell surface of a cell that has been determined to be a drug sensitive neoplastic cell of the same cell type as said candidate MDR neoplastic cell, wherein a decreased amount α 2-6 linked sialic acid bound to the surface of said candidate MDR neoplastic cell as compared to the amount of α 2-6 linked sialic acid known to be bound to the cell surface of a cell that has been determined to be a drug sensitive neoplastic cell of the same cell type as said candidate MDR neoplastic cell indicates that said candidate MDR neoplastic cell is likely to be an MDR neoplastic cell.

16. The method of claim 15, wherein determining the amount of said α 2-6 linked sialic acid bound to the surface of said candidate MDR neoplastic cell comprises measuring the amount of a sialic acid binding agent bound to said α 2-6 linked sialic acid.

17. The method of claim 16, wherein said sialic acid binding agent is selected from the group consisting of lectins and antibodies.

18. The method of claim 16, wherein said sialic acid binding agent comprises a label.

19. The method of claim 18, wherein said label is selected from the group consisting of a fluorescent label, a chemiluminescent label, a radioactive label, a magnetic label, a paramagnetic label, a promagnetic label and a colorometric label.

20. The method of claim 16, wherein said sialic acid binding agent is *Sambucus nigra* agglutinin (SNA).

21. The method of claim 15, wherein said candidate MDR neoplastic cell is selected from the group consisting of lymphoma cells, melanoma cells, sarcoma cells, leukemia cells, retinoblastoma cells, myeloma cells, glioma cells, mesothelioma cells and carcinoma cells.

22. The method of claim 15 further comprising treating said cell with a chemotherapeutic agent for the treatment of cancer.

\* \* \* \* \*

UNITED STATES PATENT AND TRADEMARK OFFICE
CERTIFICATE OF CORRECTION

PATENT NO. : 7,585,503 B2 Page 1 of 1
APPLICATION NO. : 11/094704
DATED : September 8, 2009
INVENTOR(S) : Nahid Razi It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 79 days.

Signed and Sealed this

Fourteenth Day of September, 2010

David J. Kappos
*Director of the United States Patent and Trademark Office*